US008489174B2

(12) United States Patent
Stemmer

(10) Patent No.: US 8,489,174 B2
(45) Date of Patent: Jul. 16, 2013

(54) METHOD TO DETECT A BREATHING MOVEMENT OF AN EXAMINATION SUBJECT CORRESPONDING TO SIGNAL DATA BY MAGNETIC RESONANCE

(75) Inventor: Alto Stemmer, Abenberg (DE)

(73) Assignee: Siemens Aktiengesellschaft, Munich (DE)

(*) Notice: Subject to any disclaimer, the term of this patent is extended or adjusted under 35 U.S.C. 154(b) by 373 days.

(21) Appl. No.: 12/953,805

(22) Filed: Nov. 24, 2010

(65) Prior Publication Data

US 2011/0152668 A1 Jun. 23, 2011

(30) Foreign Application Priority Data

Nov. 27, 2009 (DE) .................. 10 2009 055 961

(51) Int. Cl.
*A61B 5/05* (2006.01)
(52) U.S. Cl.
USPC ............ 600/410; 600/407; 600/413; 600/424
(58) Field of Classification Search
USPC .................................. 600/407, 410, 413, 424
See application file for complete search history.

(56) References Cited

U.S. PATENT DOCUMENTS

| | | | |
|---|---|---|---|
| 4,761,613 A | 8/1988 | Hinks | |
| 4,961,426 A | 10/1990 | Spraggins et al. | |
| 6,067,465 A | 5/2000 | Foo et al. | |
| 7,561,909 B1 * | 7/2009 | Pai et al. .................. | 600/410 |
| 7,693,569 B1 * | 4/2010 | Brittain et al. ............ | 600/413 |
| 2009/0018433 A1 | 1/2009 | Kassai et al. | |

OTHER PUBLICATIONS

"Spin-Echo M-Mode NMR Imaging," Matsuda et al., Magnetic Resonance in Medicine, vol. 27 (1992) pp. 238-246.
"Rapid NMR Cardiography With A Half-Echo M-Mode Method," Hardy et al., Journal of Computer Assisted Tomography, vol. 15 (1991) pp. 868-874.
"Self-Navigated Detection of Motion in 3D Abdominal Imaging," Brau et al., Proc. Intl. Soc. Mag. Reson. Med., vol. 14 (2006) pp. 2977.
"Extraction of Cardiac and Respiratory Motion Cycles by Use of Projection Data and Its Applications to NMR Imaging," Kim et al., Magnetic Resonance in Medicine, vol. 13 (1990) pp. 25-37.

* cited by examiner

*Primary Examiner* — Unsu Jung
*Assistant Examiner* — Joel Lamprecht
(74) *Attorney, Agent, or Firm* — Schiff Hardin LLP

(57) ABSTRACT

In a method for the detection of signal data corresponding to a breathing movement of an examination subject by magnetic resonance (MR) first and second data sets are loaded, that each include complex k-space data acquired with a navigator sequence from a common excitation volume of the examination subject. The first and second data sets are processed to identify breathing movement at the acquisition time of at least one of the data sets, by comprising a transformation of the data sets in Cartesian space and calculating a phase difference between respective complex data pointes of the data sets having the same spatial position. The processing result is stored together with a time value that depends on a point in time of the acquisition of the first data set and/or the second data set. The data acquisition, processing and storage are repeated until a series of results has been stored that maps a breathing movement of interest, and in repetition at least one of the two data sets is acquired at a different point in time than the last two data sets.

16 Claims, 7 Drawing Sheets

METHOD TO DETECT A BREATHING MOVEMENT OF AN EXAMINATION SUBJECT CORRESPONDING TO SIGNAL DATA BY MAGNETIC RESONANCE

BACKGROUND OF THE INVENTION

1. Field of the Invention

The invention concerns a method to detect a breathing movement of an examination subject corresponding to signal data by means of magnetic resonance, and a computer-readable storage medium to implement the method.

2. Description of the Prior Art

Magnetic resonance technology (in the following the abbreviation MR stands for magnetic resonance) is a known technique with which images of the inside of an examination subject (for example) can be generated. Expressed more simply, in an MR examination, consisting of one or more MR measurements, the examination subject is positioned in a comparatively strong, static, for the most part homogeneous basic magnetic field (field strengths from 0.2 Tesla to 7 Tesla or more) in an MR apparatus so that its nuclear spins (spins for short) orient along the basic magnetic field. The basic magnetic field is also termed B0 field. Radio-frequency excitation pulses are radiated into the examination subject to trigger nuclear magnetic resonances, the triggered nuclear magnetic resonances are measured and MR images (for example) are reconstructed based thereon. For spatial coding of the measurement data, rapidly switched magnetic gradient fields are superimposed on the basic magnetic field. The acquired measurement data are digitized and stored in a k-space matrix as complex numerical values. An associated MR image can be reconstructed by means of a multidimensional Fourier transformation from the k-space matrix populated with values.

In magnetic resonance imaging ("MRI") the breathing movement of a patient to be examined by means of MR can lead to image artifacts known as ghosts ("ghosting"), and/or blurring and/or intensity loss in the generated images, primarily in an examination of the organs of the thorax and the abdomen, i.e., examination regions affected by the breathing movement of the patient. Additionally the breathing motion can lead to registration errors between generated images. These artifacts can hinder a finding on the basis of these images (for example by a physician) and can lead to the situation that lesions (for example) are overlooked.

Numerous techniques exist in order to reduce artifacts resulting from breathing movement. For example, respiratory triggering and respiratory gating are two classes of methods that are compatible with a plurality of imaging or spectroscopic sequences used in MR examinations (for example) in which the achievable resolution is not limited in principle (opposite to breath-holding) and that manage without, or at least with relatively little, patient cooperation.

Respiratory gating is an MR measurement during which the breathing of the patient is detected and associated with the acquired measurement data, and the repetition rate of the MR measurement (in particular its TR, thus the time between the successive excitation of a slice) is independent of the breathing of the patient. Rather, the repetition rate is controlled by a parameter or by an additional, different physiological signal, for example an EKG. The breathing information is then used (for example) to repeatedly acquire individually measured measurement data (packets)—that, for example, were acquired during stronger breathing movement—until they have been acquired in a more peaceful phase of the breathing. Another use of the breathing information can be to acquire k-space lines that are expected to be particularly movement-sensitive or k-space lines determining the image impression in an exceptional (quiet) breathing phase (what is known as "ROPE"—"respiratory ordered phase encoding").

Respiratory triggering is a technique that synchronizes an MR measurement (an imaging MR measurement, for example) with the breathing of the freely breathing patient and attempts to acquire defined packets of measurement data only during a marked phase of the breathing cycle. The marked phase is for the most part the relatively quiet phase of the breathing cycle at the end of the expiration. The acquisition of the measurement data is thus triggered by the phase of the breathing cycle. If a specific slice is excited only once per trigger, the effective repetition rate (TR) of the measurement sequence is thus a whole-number multiple ($v=1, \ldots, k$) of the mean breathing cycle of the patient.

The detection of the breathing of the patient as a physiological signal during the measurement is a requirement for respiratory triggering and respiratory gating. The detection of the breathing can occur with a pneumatic sensor, for example. Another known possibility is to detect the breathing of the patient with MR signals, known as navigator sequences. A navigator sequence is normally a short sequence that (for example) acquires MR signals of the diaphragm from which the diaphragm position of the patient at a point of the acquisition can be extracted. The navigator sequence is interleaved with an imaging sequence (for example) that acquires the measurement data for an image acquisition, which measurement data is desired for the MR examination. The diaphragm position determined with the use of the navigator sequences hereby supplies the input signal for a trigger or gating algorithm that is used.

Relative to external sensors such as pneumatic sensors to detect the breathing, such navigator sequences have economic advantages since no additional hardware is needed. Furthermore, the use of navigator sequences is normally perceived by users as simpler or less complicated in comparison to the use of an external breathing sensor (a pneumatic sensor, for instance). Such an external sensor requires an adjustment on the patient during the measurement preparation. Such an adjustment is not needed with navigator sequences.

Navigator sequences in connection with respiratory gating and respiratory triggering are widely used, for example in cardiac imaging. Here the navigator sequence normally acquires signals of the liver dome while the imaging sequence acquires signals of the heart.

The reason for positioning the sensitivity volume of the navigator sequence through the dome of the liver is the robust optimal detection of the diaphragm edge at that location due to the strong signal difference at the transition from liver to lung. However, a difficulty arises in modern systems known as "short bore systems". These have a shorter z-FOV (FOV: "field of view") than classical MR systems. The z-FOV is the extent of the spherical or cylindrical volume inside the primary magnet of the MR system in the axial direction, i.e. along the axis of the magnet, in which the basic magnetic field $B_0$ has a specified homogeneity that is sufficient for imaging. "Short bore systems" thus have a z-FOV that is too short (for example in large patients and/or given a desired imaging in the lower abdomen or pelvis) to position both the sensitivity volume of the navigator sequence and the imaging slices within this homogeneity region FOV.

In a series of methods wherein the physiological breathing signal of a patient is derived from the movement of the diaphragm; a one-dimensional MR signal is normally acquired under a readout gradient oriented in the foot-head direction. The individual methods differ in the excitation, it conventionally being a goal of the excitation to not also excite static structures (for example the ribcage) since static structures overlap moving structures in the "navigator images" reconstructed from the one-dimensional navigator signal, which would hinder a detection of the diaphragm movement.

How such an excitation with a spin echo sequence can be achieved with an excitation slice tilted relative to the refocusing slice is described in the article "Spin-Echo M-Mode NMR Imaging" by Tetsuya Matsuda et al., appearing in the periodical "Magnetic Resonance Imaging" 27, 238-246 (1992). Only spins that are localized in the intersection surface of the two slices are thus refocused and form a spin echo that is detected under the readout gradient. A disadvantage of this method is the saturation of the magnetization in the two planes.

A second method described in "Rapid NMR Cardiography with a Half-Echo M-Mode Method" by C. Hardy, J. Pearlman, J. Moore, P. Roemer and H. Cline; J. Comput. Assist. Tomogr. 15, 868 (1991) uses what is known as a 2D RF pulse that has a cylindrical excitation profile in a gradient echo navigator sequence. This solves the saturation problem of the aforementioned method. However, this type of excitation is not particularly robust and therefore is at best conditionally suitable for clinical use.

In the prior art methods are also known that do not derive the physiological signal from the position of the diaphragm.

For example, in U.S. Pat. No. 4,761,613 an additional signal with constant phase encoding moment is acquired under every readout prephasing gradient of a spin echo sequence. These echoes, what are known as monitor echoes, are subsequently compared with a reference monitoring echo and from the comparison it is decided whether the imaging data acquired during the subsequent spin echo are used for image reconstruction or not.

In Proc. Intl. Soc. Mag. Reson. Med. 14 (2006), p 2977 a gradient echo sequence is described in which the navigator signal is acquired in a 20 µs-long time window between the slice refocusing gradient and the delayed, switched phase encoding gradient (or, respectively, readout prephasing gradient). During the navigator time window all gradients are off. The magnitude of the navigator signal from the component coil with maximum signal forms a physiological signal point. The series of signal points that is obtained by means of a series of such navigators is subsequently lowpass-filtered and used as an input signal for a respiratory gating algorithm. A disadvantage of this method is that the minimum echo time of the sequence is extended by the time separation of the slice refocusing and phase encoding gradients (or, respectively, the readout prephasing gradient). Furthermore, it is disadvantageous that a projection of the complete excitation volume is used as a navigator signal. This can lead to a dephasing of the signal given the presence of spatially inconstant B0 inhomogeneities. Furthermore, the method—like all so-called "self-gated" or "self-navigated" methods in which both navigator data and image data are acquired after one excitation pulse—is not compatible with respiratory triggering.

A similar evaluation of an acquired navigator signal via digital filtering is also described in U.S. Pat. No. 4,961,426. However, there either the navigator data are acquired under a second readout gradient after the acquisition of the image data and after a rephasing the phase encoding moment or image data and navigator data are acquired in an interleaved manner after a respective separate excitation.

How the movement of the ribcage can be extracted from projection data as a physiological signal correlated with the breathing is described in the article "Extraction of Cardiac and Respiratory Motion Cycles by Use of Projection Data and Its Applications to NMR Imaging" by W. S. Kim et al.; Magnetic Resonance in Medicine 13, 25-37 (1990). The projection data are acquired between excitation pulse and refocusing pulse of the imaging spin echo sequence.

Respiratory gating and respiratory triggering methods are used not only for imaging or spectroscopic MR examinations of the heart but also for MR examinations of the abdomen or pelvis, for example. However, in contrast to MR examinations of the heart, a detection of the breathing movement by means of navigator sequences in examinations of the abdomen and pelvis is disproportionately more difficult. One reason for this is that an excitation volume for the navigator sequences and an examination volume for the MR examination are both situated in the region of the abdomen and, in general, will overlap.

In order to reduce interference—for example saturation bands in anatomical images of a breath-triggered imaging MR examination—as a result of the navigator excitation that also acts on the examination volume, an excitation pulse of the navigator sequence may only generate a small flip angle of the excited spins so that only a small saturation enters the magnetization, for example. However, a signal that is generated with such a small flip angle has a poor signal-to-noise ratio. Furthermore, the small flip angle condition precludes spin echo techniques.

Not only can the navigator excitation can have an interfering influence on the excitation of the breath-triggered MR examination, but also the reverse may be true. For example, an evaluation of the generated navigator data can be hindered by influences of the breath-triggered MR examination. For example, the excitation of the imaging slices by an imaging sequence can generate saturation bands in the navigator image. The positions of these saturation bands may vary spatially (for example in an interleaved, multi-slice measurement) and the intensities of these saturations bands will decline over time. In the series of the navigator images in which the acquired navigator data are shown, the saturation bands are therefore structures that vary over time. These must be differentiated from those structures whose variation over time is a consequence of the breathing movement to be detected (for example structures of the diaphragm edge).

Furthermore, there is a need for methods in order to acquire data that map the breathing movement of a patient and that can be used for respiratory gating and respiratory-triggering techniques.

SUMMARY OF THE INVENTION

An object of the present invention is to provide a method and a non-transitory computer-readable storage medium with which a signal corresponding to a breathing movement of an examination subject to be examined can be obtained with certainty and without disturbing the magnetization of the examination volume significantly and which are applicable to all prevalent MR apparatuses, wherein the acquired signal can be used for a respiratory triggered or a respiratory gated MR examination.

The invention is based on the following considerations. The breathing of a patient to be examined by means of MR induces a time variation of the basic magnetic field (B0 field) of the MR apparatus used for the examination. A time variation of the resonance frequency is therefore likewise induced.

A signal generated in the patient by means of the MR apparatus and previously received by an acquisition coil of the MR apparatus is proportional to the transversal magnetization $M(t)$.

Disregarding the T2 decay, it follows from the Bloch equations that the transversal magnetization M(t) of an excited slice can be written as follows:

$$M(t) = \int_{Slice} m(\vec{x}) e^{-i\int \omega(\vec{x},\tilde{t})d\tilde{t}} d\vec{x}$$

wherein $m(\vec{x})$ describes the distribution of the magnetization in the slice and $\omega(\vec{x},t)$ describes the time-dependent deviation of the resonance frequency at location:

$$\omega(\vec{x},t) = \gamma(\vec{x}\vec{G}(\vec{x},t) + \Delta B_0^{Breathing}(\vec{x},t) + \Delta B_0^{Other}(\vec{x},t)).$$

$\gamma$ is the gyromagnetic ratio, $\vec{G}(\vec{x},t)$ stands for the gradient fields, $\Delta B_0^{Breathing}(\vec{x},t)$ stands for the deviation of the B0 field as a result of the breathing and $\Delta B_0^{Other}(\vec{x},t)$ stands for additional deviations of the B0 field that have other causes.

If an echo time of a navigator sequence—thus the time between the excitation of a signal and the time of a generated echo—is short relative to a typical time constant of a breathing movement (a human breathing cycle is approximately 4-6 seconds, for example), it can be assumed with good approximation that the deviation of the B0 field that is induced by the breathing movement is constant in this time interval. For example, gradient echo techniques in magnetic resonance are characterized by short echo times. Given an MR examination by means of a gradient echo technique, the fluctuation of the B0 field that is induced by the breathing movement thus has the result that spins at the location $\vec{x}$ accumulate an additional phase that is proportional to the deviation from the B0 field at the location and grows linearly with the time since the excitation. If it is additionally simplifying assumed that the deviation of the B0 field that is induced by breathing movement in one direction perpendicular to the readout direction is constant across an excited slice, then $$\Delta B_0^{Breathing}(\vec{x},t) = \Delta B_0^{Breathing}(x,t_n). \quad (1)$$

As a consequence of the breathing movement, acquired measurement data of an MR signal thus obtain an extra phase after a Fourier transformation in the readout direction, which extra phase is proportional to the strength of the deviation of the B0 field at the point in time of the navigator sequence with which the measurement data were acquired and rises linearly with the echo time TE:

$$\Delta\phi_{n,j}(x) = \gamma \Delta B_0(x,t_n) TE_j. \quad (2)$$

wherein n indicates the navigator sequence and j indicates an echo index. $TE_j$ is the echo time of a j-th gradient echo of the navigator sequence, $t_n$ is a time that is associated with the n-th navigator sequence.

A method according to the invention to acquire signal data corresponding to a breathing movement of an examination subject by means of magnetic resonance (MR) therefore includes the following steps:

a) load a first and second data set, which two data sets are respectively based on measurement data in the form of complex k-space data that were acquired with a navigator sequence from a common excitation volume of the examination subject, b) process the first and second data set to obtain a processing result related to the breathing movement at the acquisition time of at least one of said first and second data sets, said processing comprising a transformation of said first and said second data set in spatial space and calculating a phase difference between at least one complex data point of the first data set and a complex data point of the second data set which is associated with the same spatial position as said data point of the first data set, c) store the result from step b) together with a time value that depends on a point in time of the acquisition of the measurement data on which the first data set is based and/or a point in time of the acquisition of the measurement data on which the second data is based, d) repeat the steps a) through c) until a series of results has been stored that maps a breathing movement of interest, wherein given each repetition at least one of the two data sets loaded in step a) was acquired at a different point in time than the last two data sets loaded beforehand in step a).

As described above, a series of results that corresponds to a breathing movement that existed at the acquisition of the respective data sets can be obtained in this manner. For this purpose, it is not necessary that the data sets contain data from a region of the examination subject in which the diaphragm of the patient is situated. Rather, the location in the examination region from which the MR signals forming the basis of the data sets originate can be selected in a wide region of the examination subject that is affected by the breathing movement. For example the region in particular does not have to contain the diaphragm of the patient. Only a positioning in regions that are additionally affected by other periodic movements (for example near the heart) can incur interference.

In one embodiment, the results of the above step b) and optionally the results stored from step c) can be compared as signal data corresponding to a breathing movement of the examination subject with a trigger condition, wherein if the trigger condition is satisfied an acquisition of measurement data for an imaging or spectroscopic MR examination of a volume to be examined is triggered. The method according to the invention can thus be used for a respiratory triggering of an MR examination. A volume of the examination subject that is to be examined by means of the MR examination is thereby predetermined by an operator. In one embodiment, an excitation volume for a navigator sequence for the acquisition of first and second data sets can now be set automatically depending on the volume to be examined. The operation is thus simplified since it is no longer incumbent upon the operator to set the excitation volume of the navigator sequence such that, for example, the diaphragm edge of the examination subject is excited.

A navigator sequence with which measurement data are acquired on which the first and second data set are based generates at least one echo, for example, and samples it for the acquisition of the measurement data. If an echo time TE of the navigator sequence is thereby selected to be short relative to a time constant of a breathing movement, it can be assumed with good approximation that a deviation of the B0 field that is induced by the breathing movement is constant in this time interval TE. The Equation (1) cited above thus applies.

Program code stored in a non-transitory computer-readable storage medium according to the invention implements a method described above on a computer that is connected with magnetic resonance apparatus when it is executed on said computer.

The advantages and embodiments described with regard to the method analogously apply to the computer program.

DESCRIPTION OF THE PREFERRED EMBODIMENTS

Figure 1:
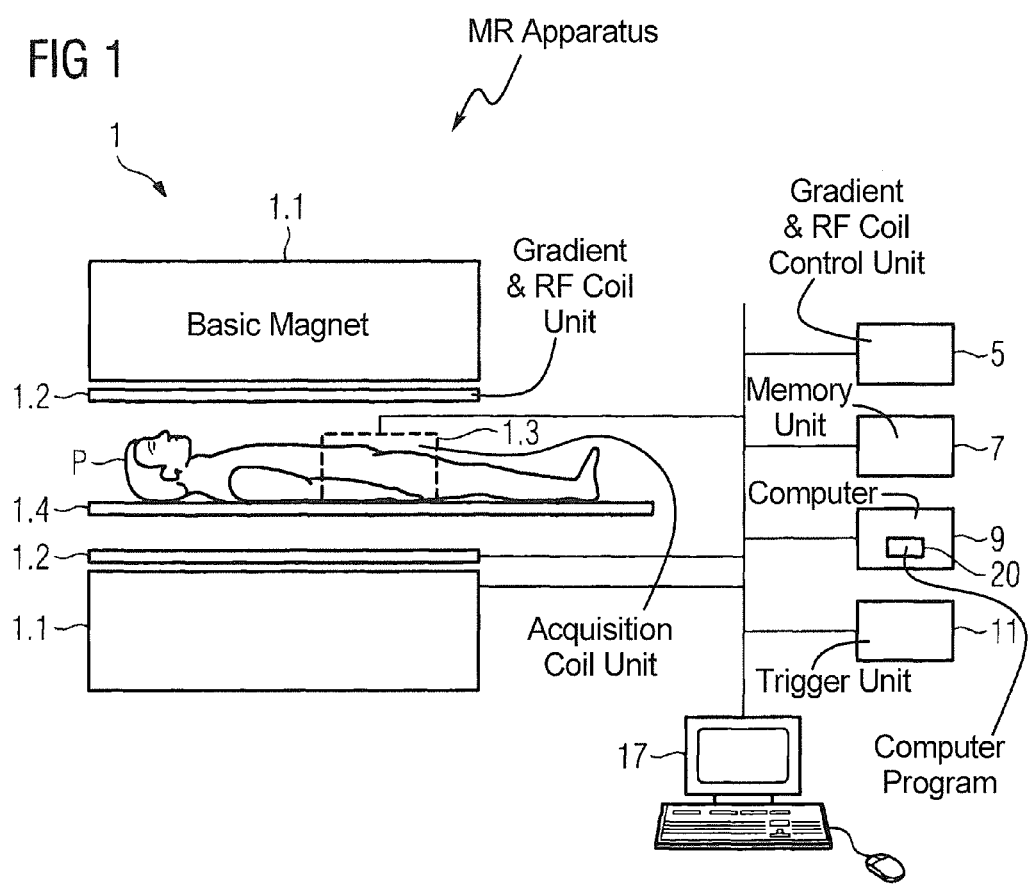
FIG. 1 schematically illustrates an MR apparatus with which the method according to the invention can be implemented.

FIG. 1 shows a schematic drawing of an MR apparatus 1 at which the method according to the invention can be implemented. The MR apparatus 1 is depicted using its basic magnet 1.1 and a gradient and RF coil unit 1.2 with which pulse sequences are executed in an examination subject (for example a patient) to be examined and MR signals are thus generated and can be acquired as measurement data. Furthermore, a receive coil unit 1.3 to acquire the measurement data is shown which comprises at least one acquisition coil. Additional components of an MR apparatus and its mode of operation are known and are not shown or explained in detail for clarity.

A patient P is borne on a patient support device 1.4 on which the patient P can be driven into and out of the examination region of the MR apparatus 1.

A breathing signal of the patient P can be detected by the MR apparatus 1 directly by means of navigator sequences wherein the patient can be situated on the patient support device 1.4 without additional limiting apparatuses on his or her body. For this MR signals are generated (for example by means of the gradient and RF coil unit 1.2) and acquired as measurement data (by means of the acquisition coil unit 1.3). The gradient and RF coil unit 1.2 and the receive coil unit 1.3 are thereby controlled by a gradient and RF coil control unit 5. The same analogously applies for an acquisition of measurement data for an imaging or spectroscopic MR examination.

The acquired measurement data, combined into data sets, are stored in a memory unit 7, for example.

Stored data sets can be loaded into a computer 9 and processed there. Results of the processing and possibly accumulating in the processing of intermediate results can in turn be stored in memory unit 7 and retrieved there again.

For example, signals corresponding to a breathing movement can be obtained as results of a processing of data sets and be stored in the memory unit 7.

Such signals can also be compared with a trigger condition by a trigger unit 11. If the trigger condition is satisfied, the trigger unit 11 can induce the gradient and RF coil control unit 5 to initiate a generation of MR signals and acquisition of corresponding measurement data for an imaging or spectroscopic MR examination.

Processing of data sets by means of the computer 9 can also take place in a conversion of the acquired measurement data into image data or spectroscopic data.

A computer program 20 that implements a method according to the invention on the computer 9 when it is executed on the computer 9 can be executed on the computer 9.

For example, calculated image data or other results or intermediate results of a processing of measurement data and/or other data pertaining to the MR examination can be displayed on a display and operating unit 17. Alternatively, inputs by a person supervising the MR apparatus can be made that, for example, pertain to a type of desired MR examination.

The division of the different units that is selected here is not to be understood as a physical division but rather as a purely illustratively division into figurative units. All cited units can be combined into a single physical unit or can be divided up in any other arbitrary manner or even be interconnected.

Figure 2:
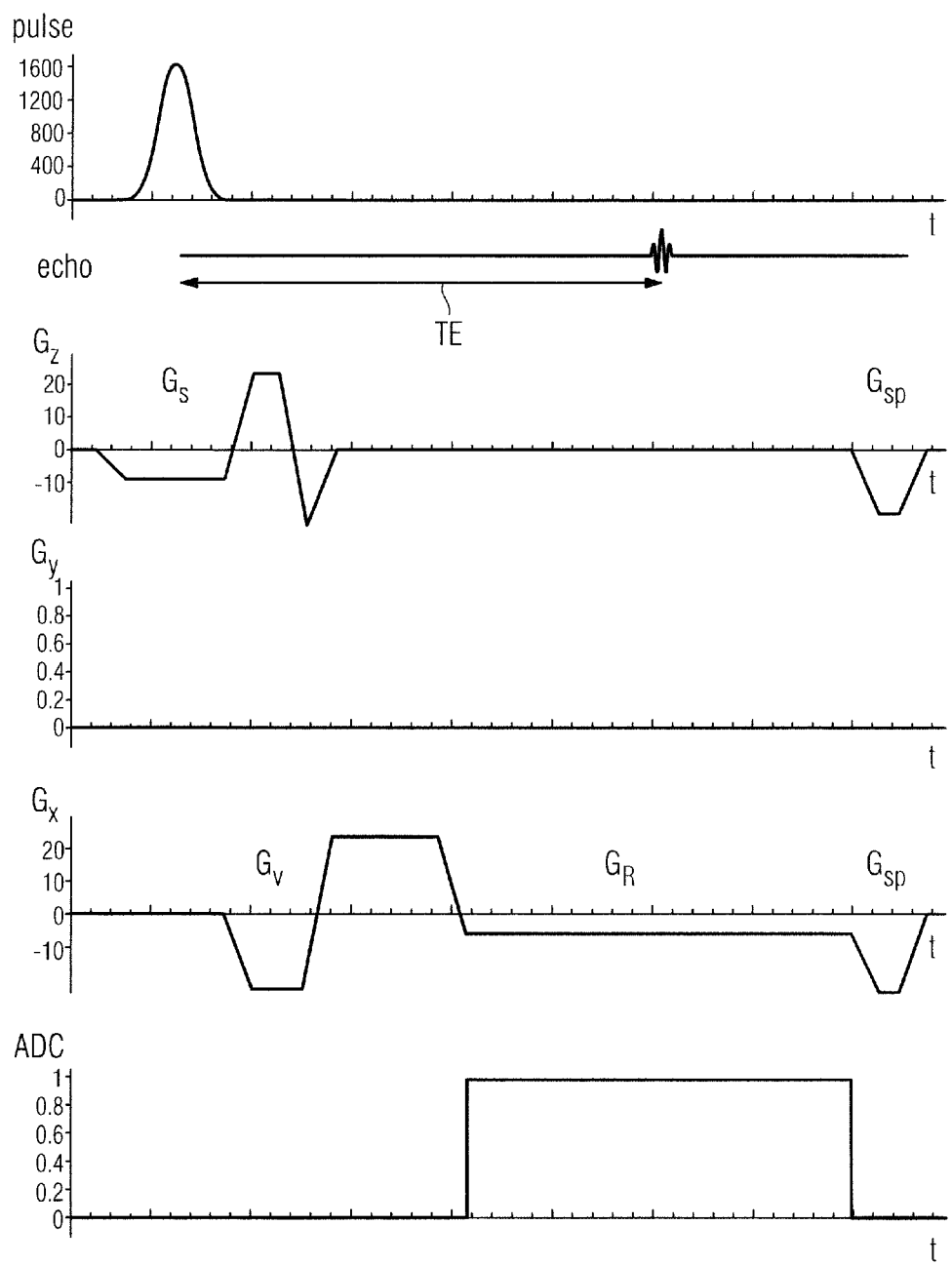
FIG. 2 is a representation of a navigator sequence that is suitable for the acquisition of measurement data from which a signal corresponding to a breathing movement can be calculated.
Figure 3:
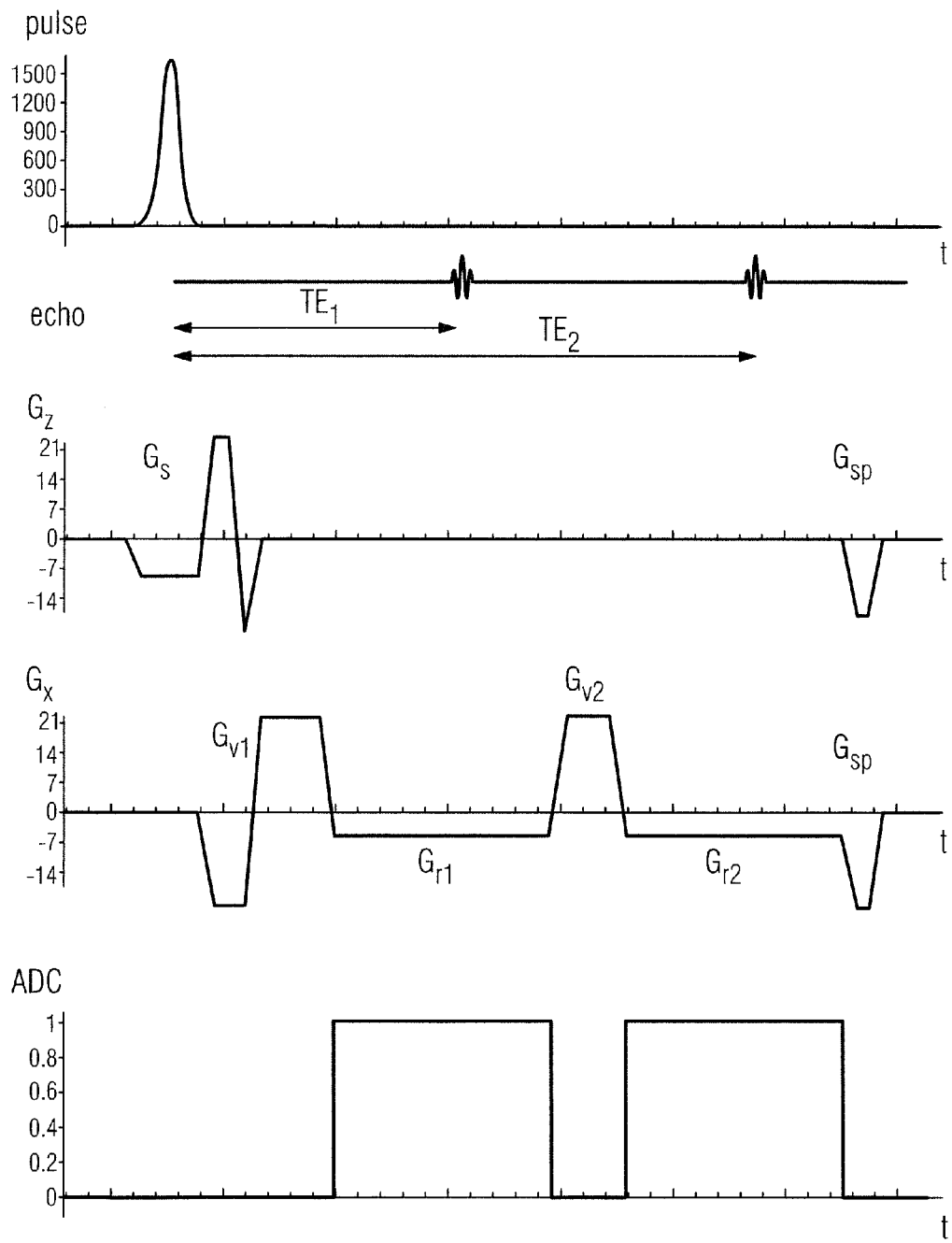
FIG. 3 is a representation of an additional navigator sequence that is suitable for the acquisition of measurement data from which a signal corresponding to a breathing movement can be calculated.

FIGS. 2 and 3 show representations of navigator sequences that are suitable for the acquisition of measurement data, from which measurement data a signal corresponding to a breathing movement can be calculated.

FIG. 3 shows a navigator sequence for the acquisition of two data sets. The shown navigator sequence is a spoiled double-echo gradient echo sequence. In comparison to a gradient echo sequence that is used for the acquisition of image data, here the phase encoding gradient and the phase refocusing gradient are absent.

An excitation pulse (line "pulse") is radiated into the examination subject with the simultaneous switching of a slice-selection gradient $G_S$ (line "$G_z$"), wherein an excitation angle achieved with the excitation pulse is chosen to be significantly smaller than is typical in (for example) imaging in order to not saturate the magnetization.

After the slice-selection gradient $G_S$, a first readout prephasing gradient $G_{V1}$ (line "$G_x$") is switched that dephases a phase of the spins. The phase of the spins that have accumulated different phases at different locations in the readout direction as a result of the first readout prephasing gradient $G_{V1}$ is subsequently rephased by switching a first readout gradient $G_{r1}$. A first gradient echo (line "echo") is generated at the point in time at which the zeroth moment of the readout prephasing gradient is compensated by the already accumulated moment of the readout gradient. The zeroth moment hereby corresponds to the area under the gradient. In FIG. 3 this is the case in the center of the first readout gradient $G_{r1}$. The gradient echo is sampled under the readout gradient and corresponding measurement data are acquired by means of at least one acquisition coil. The acquisition of the measurement data ensues in parallel with the switching of the readout gradient, as shown in the line "ADC". In the shown scheme for the first readout prephasing gradient $G_{V1}$, the first moment is also zero at this point in time. Such a flow-compensated scheme can be selected but is not necessary.

A moment accumulating in the further course of the method due to the first readout gradient $G_{r1}$ is compensated in FIG. 3 by a second readout prephasing gradient $G_{V2}$; the spins are thus dephased again. A second readout gradient $G_{r2}$ follows the second readout prephasing gradient $G_{V2}$. The second readout gradient $G_{r2}$ is identical to the first readout gradient $G_{r2}$. The peak of a second gradient echo thus falls in the center of the second readout gradient $G_{r2}$. As is described above for the first gradient echo, the second gradient echo is likewise scanned and measurement data are acquired.

The measurement data acquired during the first readout gradient $G_{r1}$ are thereby associated with a first data set and the measurement data acquired during the second readout gradient $G_{r2}$ are thereby associated with a second data set.

In an alternative embodiment (that is not also shown here) the second readout prephasing gradient $G_{V2}$ can be omitted and the sign of the second readout gradient $G_{r2}$ can be reversed. The second half of the first readout gradient $G_{r1}$ then serves as a prephasing gradient of the second gradient echo. In such a case the k-space trajectory of the two gradient echoes is opposite. This can be compensated in a reconstruction of the data in that the data points read out under the second readout gradient are sorted into a k-space matrix in the reverse direction of the data points read out under the first readout gradient.

In the scheme of a navigator sequence that is shown in FIG. 3, spoiler gradients $G_{sp}$ at the end of the navigator sequence dephase a transversal signal that still remains.

The navigator sequence that is shown in FIG. 2 differs from the navigator sequence that is shown in FIG. 3 merely by the omission of the second readout prephasing gradient $G_{V2}$ and the second readout gradient $G_{r2}$ and a correspondingly earlier switching of the spoiler gradients. Here only one data set is thus acquired since only one gradient echo is generated. To clarify the circumstance that no phase encoding gradient and no phase refocusing gradient are switched, in FIG. 2 the corresponding gradient signal (no signal) is explicitly shown in the line "$G_Y$".

Given gradient echoes the echo time—thus the time passing between an excitation pulse and an echo—is short relative to typical time constants of a breathing movement or can at least be selected so as to be. Therefore the respective echo times TE in FIGS. 2 and TE1, TE2 in FIG. 3 are also short relative to (for example) a breathing cycle of human respiration.

Figure 4:
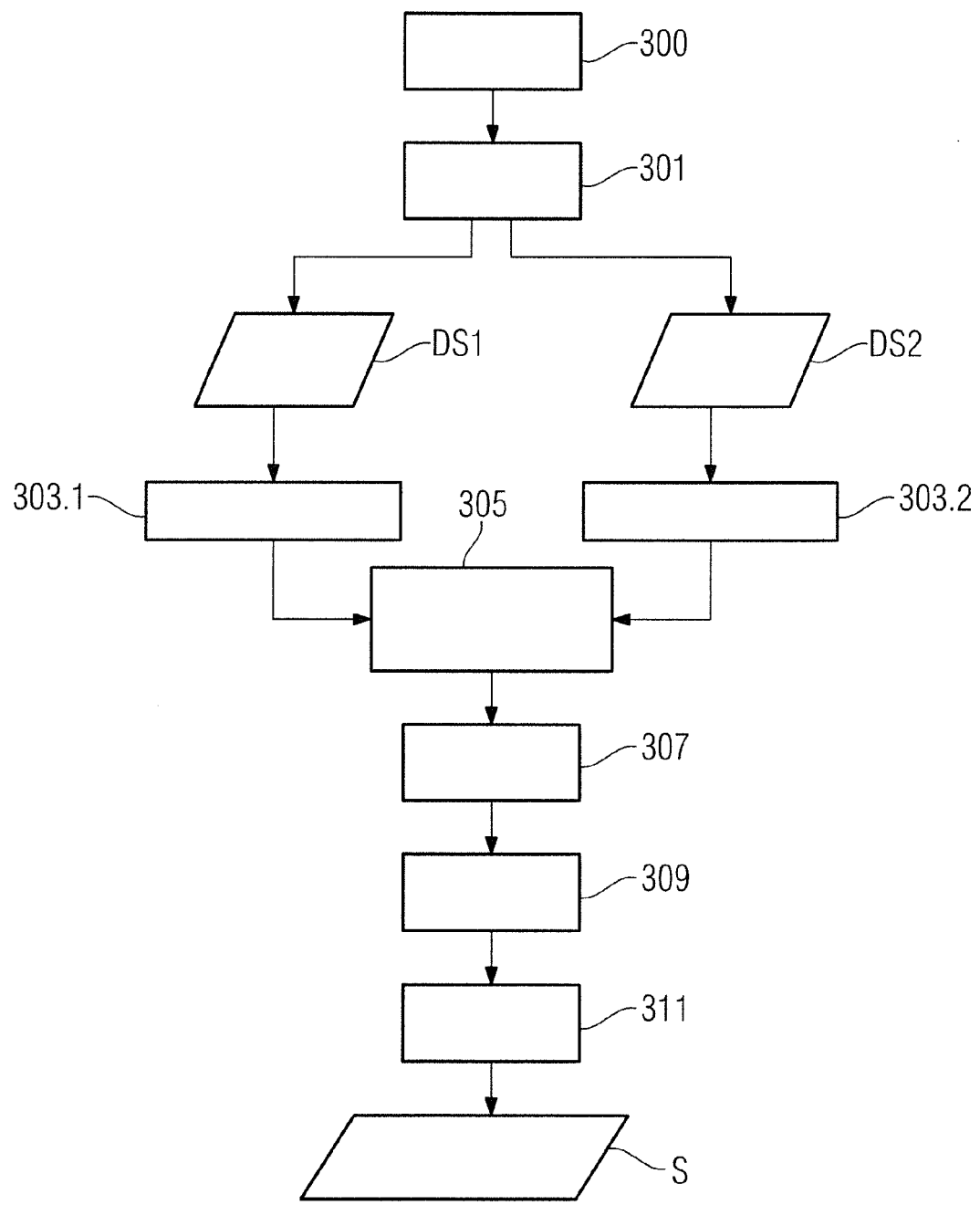
FIG. 4 is a schematic workflow diagram of a processing of a first and second data set with regard to a signal corresponding to a breathing movement.

In FIG. 4 a workflow diagram is schematically shown of a processing of a first data set "DS1" and a second data set "DS2" into a signal "S" corresponding to a breathing movement.

A position (and an orientation) of a navigator slice has initially been determined (Step 300). This occurs either manually by an operator of an MR apparatus being used or automatically as is explained later with reference to FIG. 6.

After the navigator slice is determined, this slice is excited by means of a navigator sequence, wherein at least one echo is generated and measurement data are acquired. In particular the navigator sequences presented in regard to FIGS. 2 and 3 are considered as navigator sequences. The acquired measurement data are associated with a first and second data set "DS1" and "D52".

In one exemplary embodiment the first and second data set "DS1" and "DS2" thereby respectively comprise complex k-space data points that were acquired with a navigator sequence (such as the navigator sequence shown in FIG. 3) below a first readout gradient and a second readout gradient in the time environment of the respective gradient echo.

For example, the k-space data points in a first data set "DS1" that were acquired at the first gradient echo can be sorted into a two-dimensional matrix. The first dimension can be the readout direction of the navigator sequence and thus differentiates data points that were acquired at various times; the second dimension can be, for example, a channel dimension that differentiates data points that were acquired by different acquisition coils. The k-space data points in a second data set "DS2" that were acquired at the second gradient echo can analogously be sorted into a two-dimensional matrix.

In the variants of a navigator sequence without second prephasing gradient between the first readout gradient and the second readout gradient and with opposite sign of the two readout gradients that are mentioned above in relation to FIG. 3, the sorting direction of the data points of the second echo in the readout direction is the reverse of the sorting direction of the data points of the first echo.

The processing of the first data set "DS1" and second data set "DS2" can now comprise a calculation of a respective Fourier transformation of the complex k-space data of the first and second data set (Blocks 303.1 and 303.2). The first and second data set are Fourier-transformed along the readout direction and thus converted into complex one-dimensional space data. The result is a projection of the examination subject in the direction perpendicular to the readout direction:

$$s_{n,j}(q,c) = |s_{n,j}(q,c)|e^{i\Phi_{n,j}(q,c)}, j=1, 2 \tag{5}$$

n indicates the navigator sequence with which measurement data of the data sets were acquired, j is the echo index, q is the dimension "pixel index" associated with the spatial coordinate in the readout direction, c is the index of the component coil, $|s_{n,j}(q,c)|$ designates the magnitude and $\Phi_{n,j}(q,c)$ designates the phase of the complex pixel.

As described above, among other things the phase $\Phi_{n,j}(q,c)$ additionally contains a phase accumulated as a result of the fluctuation of the B0 field that is induced by the breathing movement.

In a next Step 305 each data point of second data set $s_{n,2}(q, c)$ is multiplied with the complex conjugate $s_{n,1}^*(q, c) = |s_{n,1}(q,c)|e^{-i\Phi_{n,1}(q,c)}$ of the first data set which is associated with the same spatial position q and the same component coil c This means that a new signal matrix is calculated whose elements result as follows from the two projections $s_{n,j}(q,c)$, j=1, 2:

$$\begin{aligned} s_{n,2}(q,c)s_{n,1}^*(q,c) = \\ |s_{n,2}(q,c)||s_{n,1}(q,c)|e^{i(\Phi_{n,2}(q,c)-\Phi_{n,2}(q,c))} \end{aligned} \tag{6}$$

As is apparent in the exponents of the e-function, the phase of a pixel of the new signal matrix is equal to the phase difference of the two projections $s_{n,j}(q,c)$, j=1, 2 and therefore—as established above—correlates with a breathing movement of the examined patient.

In addition to the signal components, each individual pixel of the new signal matrix normally also contains a noise component with unspecified phase. The phase of a single pixel of the new signal matrix is therefore normally still not a physiological signal that is sufficient for robust respiratory gating or robust respiratory triggering.

To reduce the undirected noise, the signals of the different acquisition coils can be combined with one another in Step 307, for example, if more than one acquisition coil was used to acquire the original measurement data. In the simplest case, such a combination to reduce the undirected noise consists of a complex summation of the data of the new signal matrix that belong to the same spatial position q but to different acquisition coils c. This is possible since a (possibly different) phase position of signals from different acquisition coils was computationally eliminated by calculating the difference in Equation (6). If the noise correlation matrix of the individual channels is known, the summands can be weighted accordingly with a weighting R(c). For this the noise correlation matrix—and therefore the coefficients R(c)—can be calculated from measurement data (for example) which are acquired by the acquisition coils in an extra measurement using the same navigator sequence but without an excitation pulse ("pulse"). The result of the summation is a one-dimensional column vector $p_n(q)$ of complex numbers:

$$p_n(q) = \sum_c R(c) s_{n,2}(q, c) s_{n,1}^*(q, c) \quad (7)$$

Magnitude and phase of the complex elements of $p_n(q)$ are calculated and extracted in a further Step 309.

In order to achieved an additional noise suppression, in Step 311*a* weighted mean phase can be calculated in a window of the parameter q associated with a spatial coordinate, which window corresponds to a (discrete) interval in which it can be assumed that the fluctuation of the B0 field that is induced by the breathing movement is approximately constant:

$$p_n = \sum_{q \in Fenster} w_n(q) \text{ATAN2}(\text{Im}\{p_n(q)\}, \text{Re}\{p_n(q)\}). \quad (8)$$

ATAN2 designates the two-argument version of the arctangent function that is supported by most programming languages and that allows the phase in the value range $[-\pi, \pi[$ to be extracted from both of its arguments.

In equation 8, the contribution of a pixel can be weighted, for example, proportional to the square of its magnitude:

$$w_n(q) = |p_n(q)|^2 \Big/ \sum_{Window} |p_n(q)|^2. \quad (9)$$

Through such a weighting signals with better SNR are entered into the calculation of $p_n$ with greater significance.

The result of the summation in Equation (8) can be used directly as a physiological signal point $p_n$ corresponding to the breathing movement and extracted from the n-th navigator sequence. One physiological signal point is thus extracted per navigator sequence.

Depending on preference, a conversion into degrees (via multiplication with a factor $(180/\pi)$) can ensue, a normalization—for example division by the difference of the two echo times TE1 and TE2 of the navigator sequence used for the acquisition of the original measurement data of the first and second data set "DS1" and "DS2"—can ensue, or as in Equation (2) a conversion into a field strength can ensue.

It is noted that the summation in Equation (8) only delivers a usable signal if the real phase difference of corresponding pixels of the two echoes is in the range of $[-\pi, \pi[$. Otherwise it can lead to a signal cancellation if, for example, the ATAN2 function assigns a positive phase value to a pixel of the vector $p_n(q)$ whose real phase is, for example, somewhat smaller than u but assigns a negative value with an adjacent pixel whose real phase is somewhat larger than $\pi$. This situation, known as a "phase wrap", can be prevented via what is known as a "phase unwrapping" before the summation. Suitable multiples of $2\pi$ are thereby added to or subtracted from the phase of the pixels such that the phase of the column vector $p_n(q)$ is a smooth function of q. However, this process is relatively difficult and therefore error-prone, in particular given the presence of pixels that essentially contain only noise.

It results from the discussion above (Equation (2)) that the real phase difference of two pixels at spatial position x that are associated with different echo times TE1 and TE2 is proportional to the difference of the two echo times for a given fluctuation of the B0 field, if the data from which the projections are calculated are acquired with a double echo sequence:

$$\Delta B_0(x, t_n) = (\Delta \phi_{n,2}(x) - \Delta \phi_{n,1}(x))/\gamma(TE_2 - TE_1). \quad (10)$$

"Phase wraps" can accordingly be avoided via a suitable time interval of the two readout gradients. It is most simple if this adjustment of the navigator sequence ensues empirically. In particular, a smaller echo interval is selected given use of a 3T MR system than given use of a 1.5 T system, for example.

In this embodiment (using the double echo sequence of FIG. 3) the physiological signal is determined completely free of reference signals. Rather, the physiological signal is calculated via the comparison of two data sets that were acquired by means of two echoes of the same navigator sequence, and therefore in a time interval of only a few ms, interference signals (such as saturation bands) are respectively present uniformly in both data sets and thus do not generate an interfering output signal.

In another exemplary embodiment the first and second data set "DS1" and "DS2" respectively include (for example) those complex k-space data points that were acquired with a navigator sequence (such as that shown in FIG. 2) with only one gradient echo. For example, the first data set "DS1" thereby includes those respective complex k-space data points that were acquired with a current n-th navigator sequence such as that shown in FIG. 2. The second data set "DS2" comprises a reference signal, for example those complex k-space data points that were acquired as a first navigator sequence with the same single echo gradient echo sequence. Step 303.2 is advantageously implemented not for every new navigator measurement but rather only once, for example, wherein the result of Step 303.2 is stored in the first repetition and reloaded in the later repetions. The additional processing steps can be implemented identically with the double-echo variant described above. Wherein only projection data (for example) of the second echo $s_{n,2}(q,c)$ from the preceding exemplary embodiment are now respectively replaced with the projection data of the reference signal $s_{1,1}(q,c)$ and thus do not change in the course of the method. The projection data of the first echo $s_{n,1}(q,c)$ from the preceding exemplary embodiment are set equal to the projection data of the current navigator sequence.

The physiological signal $p_{n=1}$ associated with the reference sequence is therefore equal to zero.

It results from the statements made above (Equation (2)) that the signal scales with the echo time for a given fluctuation of the B0 field since a relative change of the B0 field between two navigator sequences that occurred at the times $t_n$ and $t_1$ can be measured from the phase of the projections:

$$\Delta B_0(x, t_n) - \Delta B_0(x, t_1) = (\Delta \phi_{n,1}(x) - \Delta \phi_{1,1}(x))/\gamma TE_1. \quad (11)$$

"Phase wraps" after the extraction of the phase can be accordingly avoided in that the echo time is selected to be just short enough. The adjustment of the single echo navigator sequence again ensues empirically.

Given both a use of a double-echo gradient echo sequence and a use of a single echo gradient echo sequence, the first data set and the second data set in the described methods are based on measurement data that were acquired at the same positions in the examination subject by excitation of the same excitation volume with the respective navigator sequence.

Figure 5:
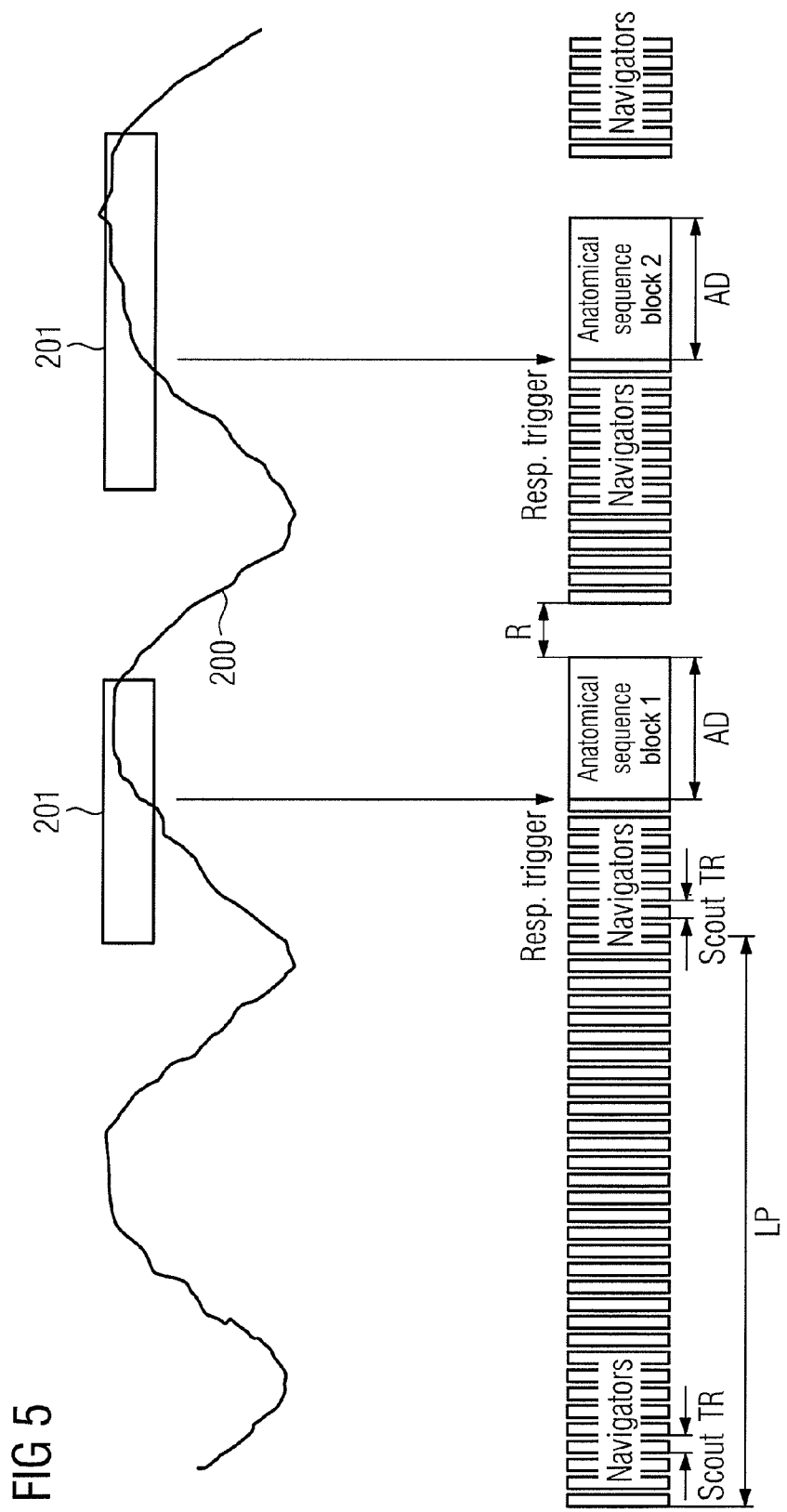
FIG. 5 is a schematic workflow diagram of a respiratory-triggered MR examination.

FIG. 5 shows a schematic representation of an example of a respiratory triggered MR examination, wherein the time curve of a sequence used for data acquisition is depicted. In this example the physiological signal is detected by means of navigator sequences. At the beginning of the sequence representing the entire MR measurement, the navigator sequence is repeated ("navigators") with constant time interval Scout TR without interruption by an imaging or spectroscopic sequence until a sufficient number of physiological data points has been detected in order to be able to implement an evaluation of the physiological breathing signal in order to be able to establish a trigger condition, for example. This phase is also designated as a learning phase ("LP") since here the individual breathing signal of the examination subject to be examined is "learned". This learning phase should not be chosen to be overly long since otherwise the total duration of the MR examination is accordingly extended. However, it should also not be selected to be overly short so that the individual breathing signal can be learned correctly. For example, if the duration of a breathing signal should be determined, it is most often necessary to detect the physiological breathing signal in the learning phase over at least one full breathing cycle. However, since the breathing signal of a breathing examination subject is not strictly periodical (rather it is subject to certain fluctuations) it is advantageous to even detect the physiological breathing signal over multiple breathing cycles in order to be able to take into account the fluctuations. This primarily applies since patients are often excited at the beginning of an examination and breathe more quickly as a result of this. Therefore a learning phase of a length of 5 breathing cycles is recommended.

An imaging phase (for example) of the MR examination begins after the learning phase "LP". In this phase the navigator sequence is likewise initially repeated ("Navigators") with constant time interval ("Scout TR") and thus a current physiological breathing signal is detected. The result of each navigator sequence is a respective physiological data point that, for example, was calculated from a phase difference as described above. The series of the last detected physiological data points allows conclusions of the current phase of the breathing. The series of the detected data points here is shown as a solid line 200 for illustrative reasons. In reality only one physiological data point is detected per navigator in the time interval of a "Scout TR". Consequently no physiological signal is present either at times at which no navigator sequence is executed. In spite of this, here it is represented as a solid signal 200 for a better understanding. As soon as a given trigger condition is satisfied ("Resp. Trigger"), no further navigator sequences are executed at first. Instead of this, the imaging sequence ("anatomical sequence block 1") is executed in the example shown in FIG. 5, meaning that an acquisition of measurement data (here imaging measurement data) is initiated and a first packet of measurement data is acquired. The triggering of the acquisition of the measurement data is designated in an abbreviated form as a trigger event in the following.

This process of the acquisition of measurement data occurs over a pre-established time interval ("Acquisition duration", "AD"). A specific, most often relatively short filling time "R" (for example of approximately 400 ms) can be inserted after the acquisition. For example, this filling time can serve to allow a disruption of the magnetization in the examination subject that was caused by the imaging sequence to at least partially decay. This is advantageous since a disrupted magnetization can negatively affect the navigator sequence. The repetition of navigator sequences is then started anew until the trigger condition is satisfied a second time, normally during the next breathing cycle of the patient. After the second trigger initiated in this manner, the imaging sequence acquires the second packet of measurement data ("anatomical sequence block 2"). This workflow is repeated until all image data are acquired.

A trigger is generated—meaning the acquisition of measurement data is initiated—if the trigger condition is satisfied. The trigger condition can thereby comprise multiple conditions that must all be satisfied. A condition can be, for example, that the patient exhales. With the sign convention that is used here this means that the result of the measured physiological data points is increasing. An additional trigger condition can, for example, be that the value of the last measured physiological breathing signal is within a pre-established acceptance window 201. In one exemplary embodiment the position of the acceptance window is automatically defined at the end of the initial learning phase LP based on the evaluated breathing signal.

Figure 6:
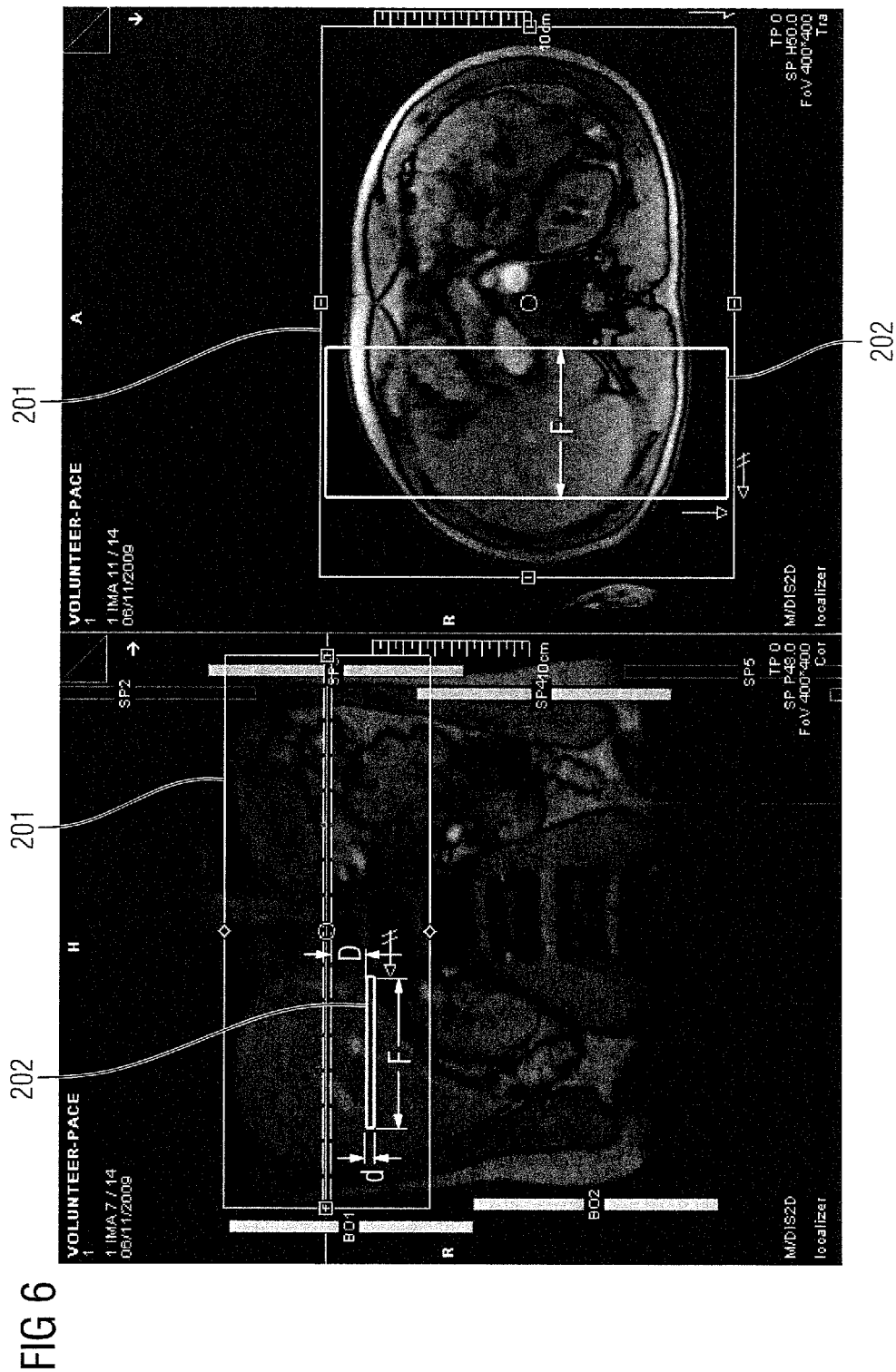
FIG. 6 is a schematic representation of an example of a respiratory-triggered MR examination.

FIG. 6 shows an illustrative representation for the positioning of an examination volume for an MR examination and an excitation volume of a navigator sequence.

The navigator sequences described above in relation to FIGS. 2 and 3 were tested in different test subjects (probands) and MR apparatuses with 1.5 T (Siemens MAGNETOM Avanto, MAGNETOM Espree) or 3 T (MAGNETOM Verio, MAGNETOM Skyra). It thereby appeared that, with the method described above, a particularly robust physiological signal correlated with the breathing is obtained in a wide range of positions of the navigator slice within the abdomen or, respectively, pelvis of the test subject—thus far removed from the diaphragm—on the basis of the determined phase difference. The method can thus also be implemented without problems for what are known as short-bore systems.

In one embodiment a positioning of an excitation volume of a navigator sequence (abbreviated as the "positioning of a navigator slice" in what follows) and the position of the window from Equation (8) are therefore automatically set relative to a position of the anatomical slices, thus to a position of an examination volume for an imaging or spectroscopic MR examination. A positioning of the navigator slice by an operator of the MR apparatus can thus be omitted.

The automatic positioning of the navigator slice can ensue in numerous ways.

For example, it can be differentiated whether the primary orientation of the anatomical slices is axial or non-axial. In the first case the orientation of the navigator slice can be selected parallel to the orientation of the anatomical slice, for example. In the second case the orientation of the navigator slice can be selected to be strictly axial with readout direction along the right-to-left direction of the patient, for example. The position of the navigator slice can now be selected as displaced by a length D (for example as shifted by approximately 15 mm) relative to the center of the anatomical slice block along the axial axis in the direction of the feet of the patient, as is well visible in the left half of FIG. 6. For example, approximately 5 mm can be selected for the thickness of the navigator slice; the excitation angle (flip angle) of the navigator sequence should be selected so as to be small, for example approximately 3 degrees, as stated above. All of these selection possibilities must only be made once by the programmer of the sequence or the automatic positioning algorithm, for example. If they are chosen, using the selected parameters the position and the orientation of the navigator slice are set automatically relative to the position and orientation of the anatomical slices. A preparation time for the MR examination is thereby markedly shortened and therefore the efficiency increases, the danger of operating error is reduced and the operator of the MR apparatus does not need to be trained in navigator positioning, which in the prior art comprises multiple work steps and therefore is very time-consuming.

In the example shown in FIG. 6 the field of view of the projection is 256 mm given a pixel size of 1 mm (thus 256 pixels in total). To avoid aliasing artifacts, 100% readout oversampling was used (thus an effective field of view of 512 mm and acquisition of 512 data points under every readout gradient). 92 mm was selected for the width of the window 202 from Equation (8). The window 202 is automatically centered in the right half of the field of view.

FIG. 6 shows the result of the automatic positioning of the navigator slice and the window from Equation (8). A coronal image, what is known as a "localizer image" is shown in the left half of FIG. 6 and an axial localizer image is shown in the right half of FIG. 6, in which images an operator of the MR apparatus defines (among other things) the position and orientation of the anatomical slices. The anatomical slice block 201 is displayed as boxes 201 in both "localizer images".

The navigator slice is automatically set by the system relative to the position and orientation of the anatomical slice block 201. Here the navigator slice is visualized by the box 202 whose extent in the axial direction is equal to the slice thickness d of the navigator excitation. In the readout direction (right-left direction) the position and extent of the window from Equation (8) contains no static structures. The current excitation volume of the navigator is a slice that contains the indicated box 202. The shown extent of the box 202 in the anterior-posterior direction (from top to bottom in the right half of FIG. 6) has no physical meaning but rather should illustrate that the complete volume is projected.

As already mentioned, there is significant freedom in the automatic positioning. For example, it is also conceivable to position the navigator slice outside of the volume detected by the anatomical slice block given an axial primary orientation of said anatomical slice block. In this way a mutual interference of imaging sequence and navigator sequence is precluded and the choice of the excitation angle of the navigator sequence is free.

The described method to acquire signal data corresponding to a breathing movement of an examination subject from data sets acquired by means of a described navigator sequence operates robustly in a wide range of positions of the navigator slice within the abdomen or pelvis.

Figure 7:
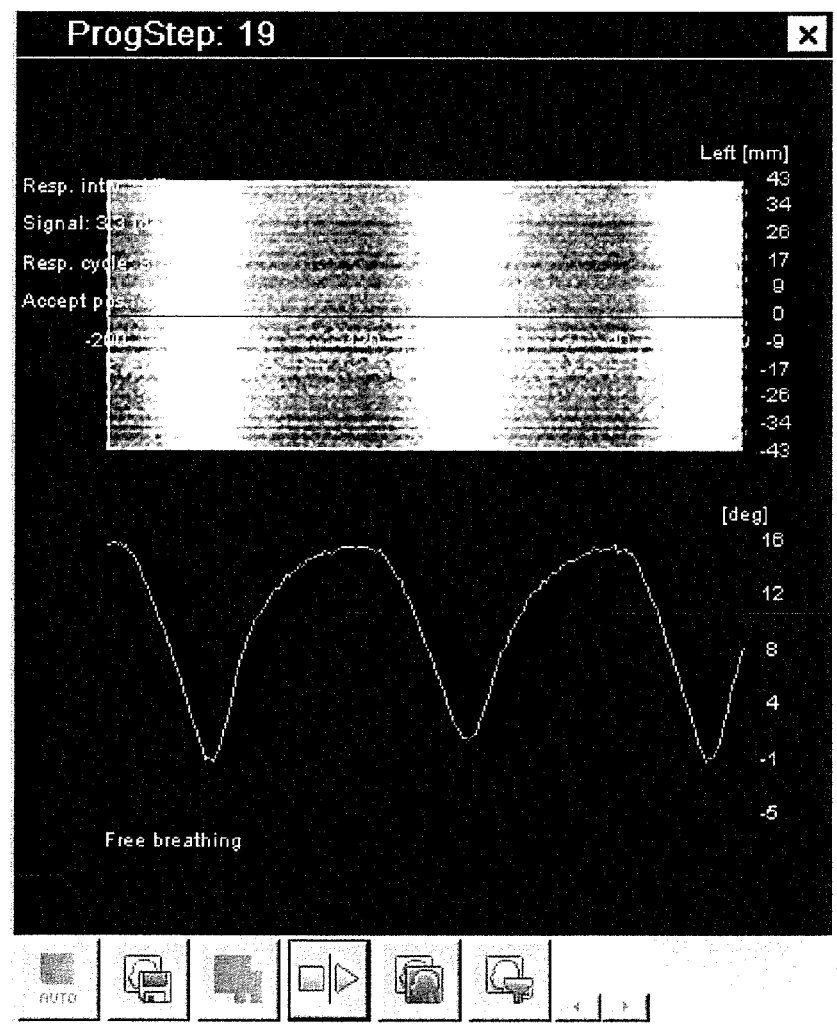
FIG. 7 is an illustrative representation of the positioning of an examination volume for an MR examination and the excitation volume of a navigator sequence which is automatically set depending on the position of examination volume.

Shown in FIG. 7 is one possibility of a display of the calculated results of the method according to the invention, for example on a display and operating unit 17 from FIG. 1. For example, such a display can be presented to an operator for information during a breath-triggered MR examination. Here the greyscale image thereby shows the phase of the vector $p_n(q)$ from Equation (7) in the upper region of FIG. 7. The result of Equation (8) corresponding to a breathing movement is indicated in the lower region. Each column corresponds to the representation of a navigator sequence. The time axis runs from left to right, meaning that the right most column of the image corresponds to the last navigator sequence. As soon as a new navigator sequence is present, the image can be shifted by one column to the left so that the result of the navigator sequence that was previously associated with the left most column is no longer shown and the right most column is free to depict the result of the navigator sequence that is now most current. For the observer the impression arises that the image runs from right to left.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to detect signal data corresponding to a breathing movement of an examination subject by magnetic resonance (MR), comprising the steps of:
   a) loading a first data set and second data set into a computerized processor, said first and second data sets respectively being based on complex k-space data acquired with a navigator sequence from a common excitation volume of an examination subject in a magnetic resonance data acquisition unit;
   b) processing the first and second data sets in said processor to obtain a processing result related to the breathing movement at the acquisition time of at least one of said first and second data sets, said processing comprising a transformation of said first and said second data set in spatial space and calculating a phase difference between at least one complex data point of the first data set and a complex data point of the second data set which is associated with the same spatial position as said data point of the first data set;
   c) electronically storing the processing result from step b) together with a time value that depends on at least one of a point in time of acquisition of the k-space data on which the first data set is based and a point in time of acquisition of the k-space data on which the second data is based; and
   d) repeating steps a) through c) until a series of processing results has been stored that maps a breathing movement of interest and, in each repetition acquiring at least either the first or second data set loaded in step a) at a different point in time than the first and second data set loaded in previous repetition of step a).

2. A method as claimed in claim 1 comprising employing a navigator sequence with which the k-space data are acquired on which the first and second data set are based that generates at least one echo and scans every echo for the acquisition of the k-space data under a readout gradient.

3. A method as claimed in claim 2 comprising processing the first and second data sets by calculating respective Fourier transformation along the readout direction of the complex k-space data of the first and second data sets and thereby obtain a new first and a new second data set where different data points in the new first data set correspond to different spatial positions along the readout direction and different data points in the new second data set correspond to different spatial positions along the readout direction.

4. A method as claimed in claim 3 comprising processing the first and second data sets obtained after the Fourier Transformation by a pairwise complex conjugate multiplication of complex numbers in the first and the second data set which correspond to the same spatial position.

5. A method as claimed in claim 2 comprising acquiring k-space data on which the first and second data sets are based respective navigator sequences using at least two acquisition coils.

6. A method as claimed in claim 5 comprising processing the k-space data acquired by said different acquisition coils separately from one another in order to obtain new data sets, said processing comprising respective Fourier Transforms along the readout direction, and in which the phase of a data point of the new data set is proportional to a phase difference of those data points of the Fourier transformed first and second data sets that correspond to the same spatial position and that were processed with one another.

7. A method as claimed in claim 6 comprising processing the data points in said new data set as a combination of data points acquired by said different acquisition coils, said combination comprises a summation across said different acquisition coils.

8. A method as claimed in claim 7 comprising processing the data set obtained after said summation across said different acquisition coils as a summation across a dimension associated with a spatial coordinate in a predetermined interval in the readout direction of the navigator sequence.

9. A method as claimed in claim 8 comprising weighting the summands in the respective summation.

10. A method as claimed in claim 1 comprising comparing at least one of the results from step b) and results stored from step c) as signal data corresponding to a breathing movement of an examination subject, with a trigger condition, and upon satisfaction of the trigger condition, initiating an acquisition of measurement data for diagnostic imaging or spectroscopic MR examination of an examination volume of the subject.

11. A method as claimed in claim 10 comprising predetermining said examination volume by an operator, and setting the excitation volume for the navigator sequence for acquisition of first and second data sets automatically depending on the volume to be examined.

12. A method as claimed in claim 1 comprising using at least one of the results from step b) and results stored from step c) as signal data corresponding to a breathing movement of an examination subject, for a respiratory gated diagnostic imaging method or a respiratory gated spectroscopic method during an MR examination of an examination volume of the subject.

13. A method as claimed in claim 12 comprising predetermining said examination volume by an operator, and setting the excitation volume for the navigator sequence for acquisition of first and second data sets automatically depending on the volume to be examined.

14. A method as claimed in claim 1 comprising employing a navigator sequence to acquire the k-space data on which the first and second data sets are based that is a gradient echo sequence that generates and samples at least one gradient echo.

15. A method as claimed in claim 1 comprising employing a navigator sequence to acquire the k-space data on which the first and second data sets are based that generates and samples two echoes, and basing the first data set on k-space data acquired during a first of said two echoes and basing the second data set on k-space data acquired during a second of said two echoes.

16. A non-transitory computer-readable storage medium encoded with programming instructions, said storage medium being loaded into a computerized processor of a magnetic resonance system, and said programming instructions causing said computerized processor to:
  a) receive a first data set and second data set, said first and second data sets respectively being based on complex k-space data acquired with a navigator sequence from a common excitation volume of an examination subject in a magnetic resonance data acquisition unit;
  b) process the first and second data sets to obtain a phase difference of a phase of the first data set and a phase of the second data set or a value proportional to said phase difference as a processing result;
  c) electronically store the processing result from step b) together with a time value that depends on at least one of a point in time of acquisition of the k-space data on which the first data set is based and a point in time of acquisition of the k-space data on which the second data is based; and
  d) repeat steps a) through c) until a series of processing results has been stored that maps a breathing movement of interest with, in each repetition acquiring at least the first or the second data set loaded in step a) at a different point in time than the first and second data set loaded in previous repetition of step a).

* * * * *